United States Patent [19]

Kelman

[11] Patent Number: 4,808,181
[45] Date of Patent: Feb. 28, 1989

[54] INTRAOCULAR LENS HAVING ROUGHENED SURFACE AREA

[76] Inventor: Charles D. Kelman, 269 Grand Central Pkwy., Floral Park, N.Y. 11005

[21] Appl. No.: 83,635

[22] Filed: Aug. 7, 1987

[51] Int. Cl.$^4$ ............................................. A61F 2/16
[52] U.S. Cl. ..................................................... 623/6
[58] Field of Search ........................................... 623/6

[56] References Cited

U.S. PATENT DOCUMENTS

| 4,343,050 | 8/1982 | Kelman | 623/6 |
| 4,449,257 | 5/1984 | Koeniger | 623/6 |
| 4,605,409 | 8/1986 | Kelman | 623/6 |

Primary Examiner—Richard J. Apley
Assistant Examiner—James Prizant
Attorney, Agent, or Firm—Henry Sternberg; Bert J. Lewen

[57] ABSTRACT

Intraocular lens for implantation in the posterior chamber of an eye, following extracapsular removal of the natural eye lens, including a lens assembly having an anterior surface formation and a posterior surface formation, at least a portion of the posterior surface formation constituting a planar contact region adapted to be seated against the adjacent planar tissue surface of the posterior capsule to form a connection interface for permanent anchoring of the lens assembly thereat, the contact region being provided with a roughened surface area defined by a series of ordered narrow linear depressions therein extending generally transversely of the plane of the contact region, for accelerated adhesion of the tissue of the adjacent posterior capsule part to the depressions and enhanced anchoring of the lens assembly to the posterior capsule part, to prevent dislodgment of the implanted intraocular lens.

15 Claims, 2 Drawing Sheets

U.S. Patent  Feb. 28, 1989  Sheet 1 of 2  4,808,181
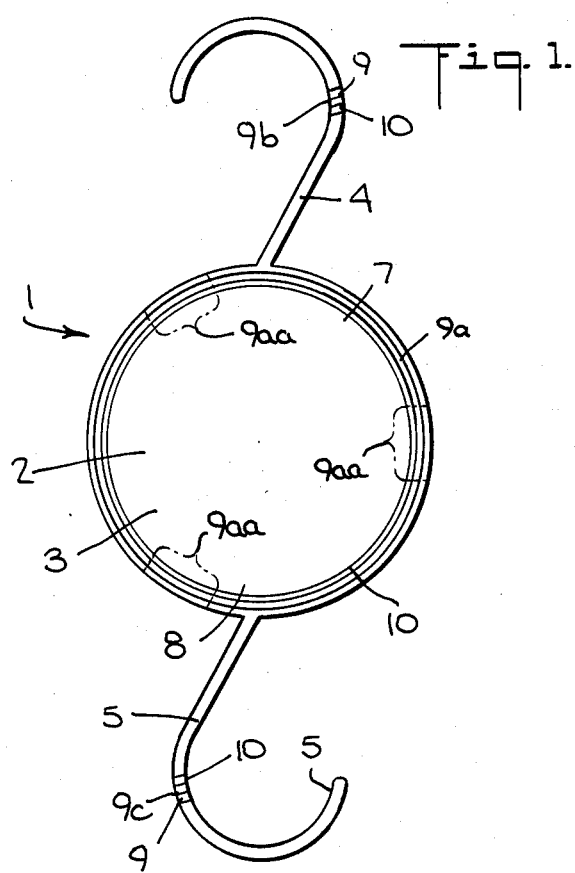
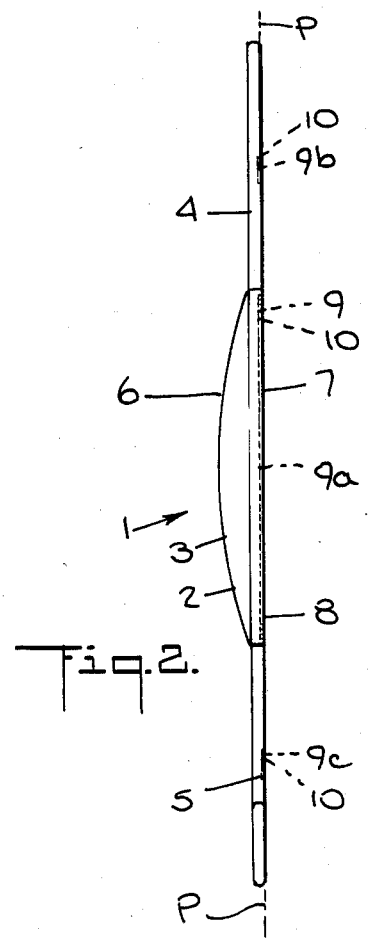
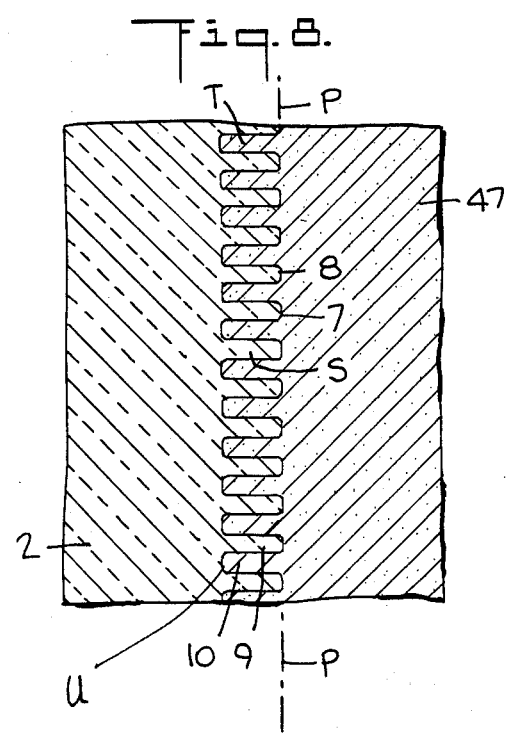
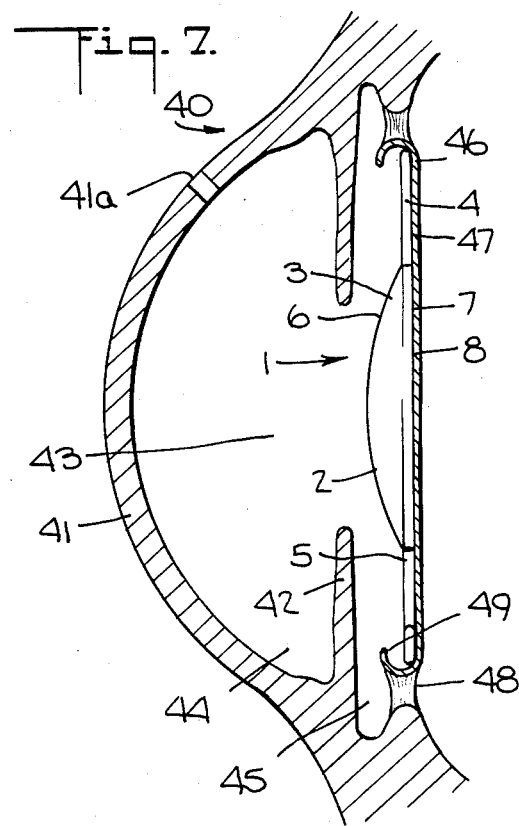

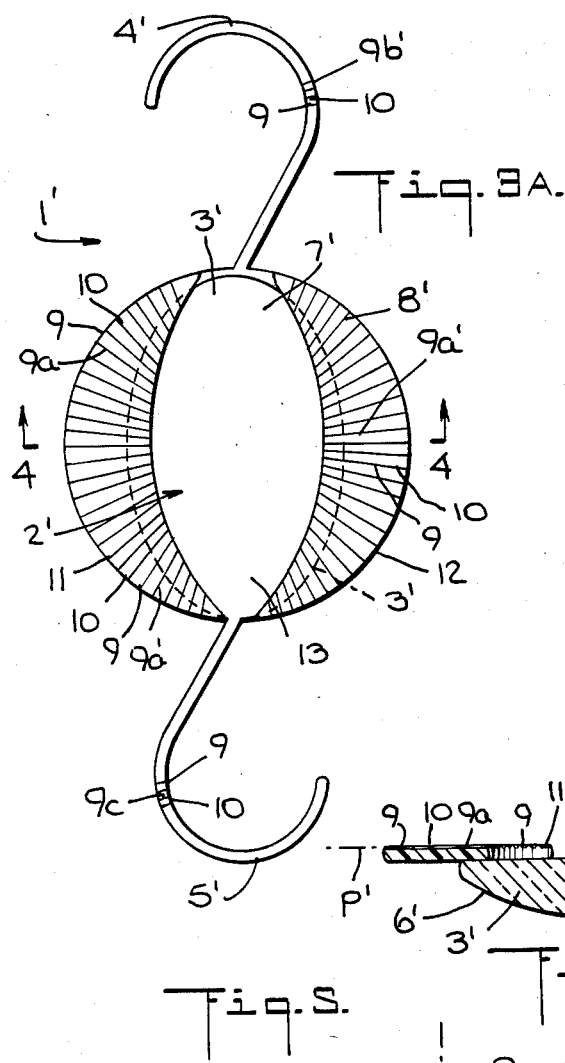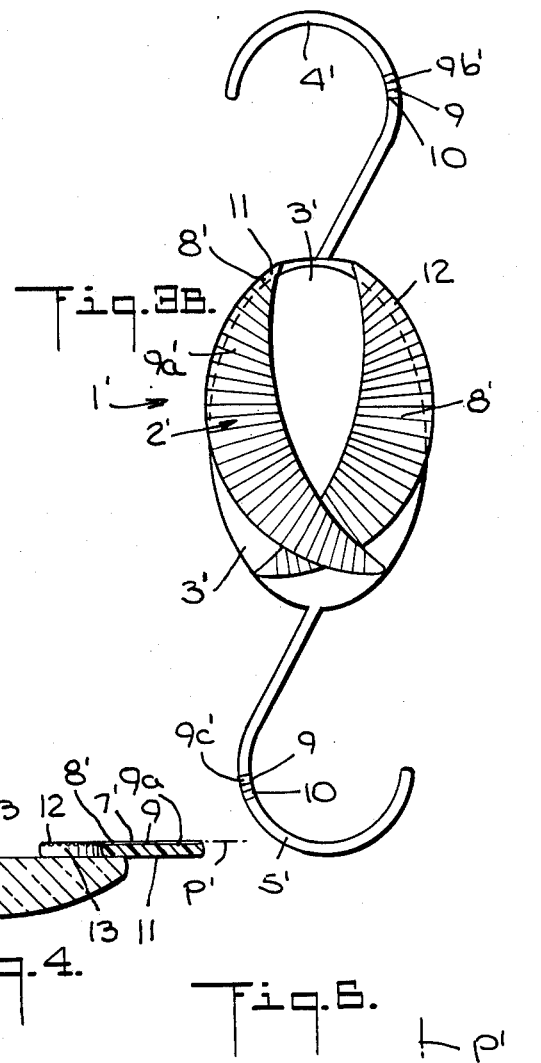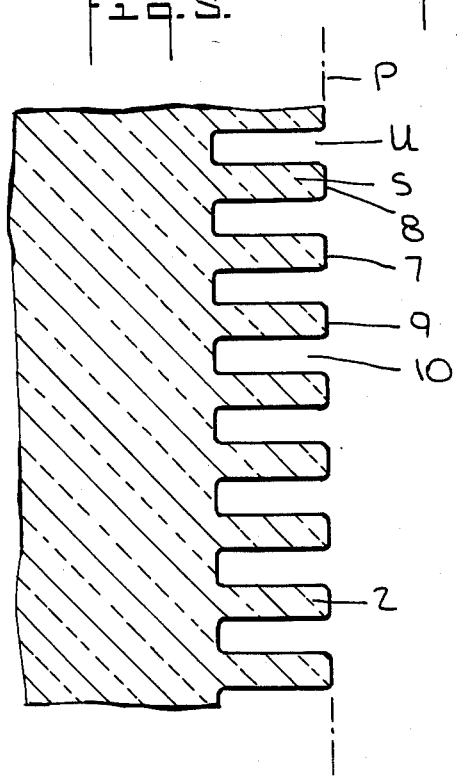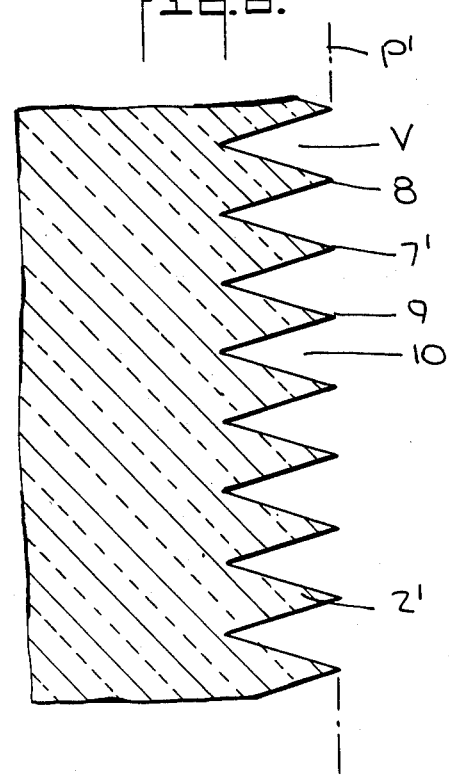

INTRAOCULAR LENS HAVING ROUGHENED SURFACE AREA

FIELD AND BACKGROUND OF THE INVENTION

The present invention relates to an intraocular lens having a roughened surface area, and more particularly to an artificial intraocular lens for implantation in the posterior chamber of an eye, after extracapsular removal of the natural eye lens, wherein the roughened surface area serves to accelerate the adhesion of the adjacent tissue to the lens and enhance the anchoring of the lens to such adjacent tissue, to prevent dislodgment of the implanted lens.

For treatment of conditions such as natural eye lens cataracts, a known eye surgery procedure is to remove the cataracted lens through an incision in the wall of the cornea of the eyeball, and replace it by an artificial intraocular lens as an internal implant lens. One specific surgical procedure involves the extracapsular removal of the natural eye lens, leaving portions of the posterior lens capsule intact. Such intact posterior portions may then conveniently serve as an anchoring site for the intraocular lens to be implanted in the eye.

U.S. Pat. No. 4,605,409 to Kelman discloses an intraocular lens having a small size optic and flexible haptics for the stated purposes as well as deformable masking means such as laterally disposed generally flat planar wings, which mask the side edge portions of the optic for specifically overcoming the problem of the edge glare effect of otherwise scattered incoming light rays at the peripheral marginal regions of such small size lens. The masking effect of the wings is achieved by leaving the flat surfaces of the wings in rough, unground condition, or by coating one of the surfaces of each wing with an opaque coating.

It is known in the art that, because of the undesired possibility of materials in the eye, for example fibrin, collecting on an optic, such as one made of silicone material, due to the surface characteristics of such silicone, it is preferred instead to make the optic of a material such as polymethylmethacrylate (PMMA) which is not only relatively rigid but which also does not have properties which cause any of the materials in the eye to adhere thereto. It is further known that the physical properties of polymethylmethacrylate are such that fibrin and other materials in the eye are constantly washed away from its surface rather than adhering thereto.

U.S. Pat. No. 3,458,870 to Stone, Jr. concerns a structural corneal implant in the form of a curved annular holding member having a central opening containing a removable lens member, arranged such that the holder is seated in an incision pocket parallel to and intermediate the anterior and posterior surfaces of the corneal wall in the manner of a sandwich. The periphery of the annular holder is provided with a plurality of circular rows of holes extending completely therethrough to permit bilateral anchoring ingrowth of corneal stroma to fill the holes for providing a gross mechanical structural interconnection rather than one utilizing surface adhesion.

U.S. Pat. No. 4,304,012 to Richard is to the same general effect, in this case providing the haptics with such anchoring holes completely therethrough for positioning the intraocular lens in contact with the iris or other eye tissue to permit such ingrowth of tissue completely through the holes. The holes are stated to have a diameter in the range of 0.002-0.006 inches (0.0508-0.1524 mm), and the mechanical structural interconnection is described as one in which the live tissue which grows through the given hole develops an enlarged rivet head like protrusion on the exposed side thereof and provides a "riveting" effect for a stronger attachment than otherwise.

It would be desirable to provide a, preferably deformable, intraocular lens for implantation in the posterior chamber of an eye, following extracapsular removal of the natural eye lens, which would permit accelerated adhesion of the tissue of the adjacent portion of the posterior capsule to the lens and enhanced anchoring of the lens thereto, without the need for gross structural formations in the lens such as a plurality of holes extending completely therethrough and requiring mechanical anchoring tissue ingrowth completely through the holes in gross manner to achieve the desired connection.

SUMMARY OF THE INVENTION

It is among the objects and advantages of the present invention to overcome the drawbacks and deficiencies of the prior art, and to provide an artifical intraocular lens for implantation in the posterior chamber of an eye, after extracapsular removal of the natural eye lens, the intraocular lens having at least one roughened surface area for accelerated adhesion thereto of tissue of the adjacent posterior capsule and enhanced anchoring of the implant lens to such tissue of the posterior capsule, to prevent dislodgment of the implanted lens.

It is among the additional objects and advantages of the present invention to provide an intraocular lens of the foregoing type, in which the roughened surface area is defined by a series of ordered narrow linear depressions or furrows, promoting surface adhesion, rather than gross mechanical interconnection, for achieving such anchoring, and within an accelerated period of time, of at most several hours, from the completion of the implanting of the intraocular lens in place in the interior of the eye.

It is among the further objects and advantages of the present invention to provide an intraocular lens of the stated type, which is relatively safe and non-irritating to the eye in use, and which can be made from readily available materials, and preferably of flexible, temporarily deformable, construction to permit its deformation to reduce its apparent girth for insertion into an eye through a minimum size corneal incision, yet which will readily return to its original, expanded and undeformed state, while retaining its desired optical characteristics, once it is inside the eye, enabling the lens to be seated properly by the surgeon in the posterior chamber adjacent the posterior capsule.

According to the present invention, an artificial intraocular lens is provided for implantation in the posterior chamber of an eye, following extracapsular removal of the natural eye lens. The intraocular lens comprises a lens assembly having an anterior surface formation and a posterior surface formation, at least a portion of the posterior surface formation constituting a planar contact region adapted to be seated against the adjacent planar tissue surface of the posterior capsule to form a connection interface for anchoring the lens.

The contact region is advantageously provided with at least one roughened surface area defined by a series of ordered narrow linear depressions or furrows therein extending generally transversely of the plane of the contact region, for accelerated adhesion of the tissue of the adjacent lens posterior capsule wall part to the depressions and enhanced anchoring of the lens assembly to the lens posterior capsule wall part, to prevent dislodgment of the implanted intraocular lens.

Favorably, a plurality of such roughened surface areas may be provided at corresponding spaced apart local sites on the contact region.

The lens assembly may include an optic or lens body comprising the contact region, such that the roughened surface area is located on the contact region at the periphery of the optic, for example as an annulus extending peripherally around the optic, or as individual spaced apart segment like arcs of an interrupted annulus extending peripherally around the optic.

Additionally, the lens assembly may include an optic provided with a pair of opposed haptics comprising portions of the contact region, such that at least one roughened surface area is located on a corresponding contact region portion of each haptic.

Furthermore, the lens assembly may include an optic provided with a pair of laterally disposed light ray modifying wings comprising portions of the contact region, such that at least one roughened surface area is located on a corresponding contact region portion of each wing.

BRIEF DESCRIPTION OF THE DRAWINGS

Other and further objects and advantages of the present invention will become apparent from the within specification and accompanying drawings, in which:

FIG. 1 is a plan view of the back or posterior side of an artificial intraocular lens having an optic and haptics, and provided with a roughened surface area in the form of a peripheral annulus according to one embodiment of the present invention;

FIG. 2 is a side view of the embodiment of FIG. 1;

FIGS. 3a and 3b are plan views of the back or posterior side of an intraocular lens having an optic and haptics, as well as one form of known glare effect preventing masking wings, termed a "Phaco Fit" lens assembly, showing the wings in normal expanded position in FIG. 3a and in temporary overlapping contracted position in FIG. 3b, the assembly being provided with roughened surface areas on the wings according to another embodiment of the present invention;

FIG. 4 is a sectional view taken along the line 4—4 of FIG. 3a;

FIGS. 5 and 6 are corresponding enlarged exaggerated schematic sectional views of two different embodiments of the roughened surface area provided on the lens assembly according to the present invention;

FIG. 7 is a schematic sectional view of an eyeball showing one possible way in which the intraocular lens of the present invention may be positioned in the eye at the posterior wall part of the lens capsule, following extracapsular removal of the natural eye lens and anterior wall part of the lens capsule; and FIG. 8 is an exaggerated schematic sectional view of a portion of the implanted lens in contact with the posterior wall part of the lens capsule, illustrating the arrangement of the surface adhesion of the live tissue to the roughened surface area of the implanted lens according to the present invention.

DESCRIPTION OF THE PREFERRED EMBODIMENTS

Referring to the drawings, and initially to FIGS. 1-2, an artificial intraocular lens 1, according to one embodiment of the present invention, is shown (which is either rigid, e.g. made of PMMA, or deformable, e.g. made of silicone, such that the latter type lens may be deformed into a reduced girth form for insertion into the interior of an eye through a corneal incision of minimum size), as an implant for replacing the natural lens, such as a cataracted lens, by way of surgical procedures well known to those skilled in the art.

Lens 1 is generally of the conventional type, comprising a composite lens assembly 2 having a preferably round or circular central light focusing lens body or optic 3, desirably provided with a symmetrical pair of position fixation means or haptics 4,5 or the like, i.e. oppositely disposed outwardly flaring resilient lens seating appendages. Optic 3 is preferably formed of plastic material as aforesaid, and haptics 4,5 are likewise preferably formed of plastic material.

Haptics 4,5 or the like may be integrally connected to optic 3, and are used for embracing the adjacent portions of the eye interior, and more specifically in connection with the objects and advantages of the present invention, for aiding the seating of lens 1 in the posterior chamber adjacent to portions of the posterior capsule, i.e. after extracapsulary removal of the natural eye lens through an incision in the cornea followed by insertion therethrough of the intraocular lens for such seating by the surgeon.

Lens assembly 2 has a front or anterior surface formation 6, collectively encompassing the corresponding front or anterior surfaces of optic 3 and haptics 4,5, and a back or posterior surface formation 7, likewise encompassing the corresponding back or posterior surfaces of optic 3 and haptics 4,5.

For the purposes of the present invention, as may be appreciated from FIG. 2, at least a portion of posterior surface formation 7 is constituted as a planar contact region 8, which is adapted to be seated against the adjacent planar tissue of the eye in the posterior chamber, as for example the posterior wall part of the lens capsule, to form a connection interface for mechanical anchoring of lens assembly 2 thereat. More significantly, contact region 8 is provided with at least one roughened surface area 9, such as area 9a, 9b and/or 9c, each of which is defined by a series of ordered narrow linear furrows or depressions 10 therein extending generally transversely of the plane P of contact region 8.

Depressions 10 efficiently serve to achieve a primary object and advantage of the present invention, in facilitating accelerated adhesion of the adjacent tissue, e.g. the tissue of the lens capsule posterior wall part, to depressions 10 and enhanced ordered mechanical anchoring of lens assembly 2 to the lens capsule posterior wall part, so as to prevent dislodgment or displacement of the so implanted intraocular lens 1 by accident, slippage, or otherwise during normal use.

Preferably, a plurality of roughened surface areas 9 is provided at corresponding local sites on contact region 8, such as area 9a located at the periphery of optic 3 and outwardly beyond the primary optical light ray transmitting central portion thereof, and/or area 9b and/or 9c located at a suitable point on haptic 4 and/or 5, as the case may be.

Where roughened surface area 9a is present, it may be disposed in the shape of a continuous ring or annulus extending peripherally around optic 3 as shown in FIG. 1, or alternatively in the shape of individual spaced apart segment like arcs 9aa (shown schematically in phantom as braced regions in FIG. 1) of an interrupted ring or annulus extending peripherally around optic 3 in a manner analogous to the continuous annulus shown in solid line in FIG. 1. In the interrupted annulus instance, at least three such segment like arcs 9aa are preferably provided in equidistant spaced relation to one another to assure more efficient balanced anchoring of lens assembly 2 in place.

Where roughened surface area 9b or 9c is present, it may be disposed at any suitable location on the corresponding haptic 4 or 5, and where both areas 9b and 9c are present, the ordered linear furrows or depressions 10 thereof are favorably oriented at an angle to each other as shown in FIG. 1, not only to assure more efficient seating of lens assembly 2 in place, but also inhibition of any incipient tendency of lens assembly 2 to rotate about its center, i.e. in a direction roughly parallel to the linear direction of the ordered depressions 10.

Where roughened surface areas 9a, 9b and 9c are all present, the collective advantages of their conjoint inclusion are accordingly achieved.

FIGS. 3a, 3b and 4 show another embodiment of an artificial intraocular lens 1' of otherwise conventional type, termed a "Phaco Fit" lens, which is analogous to lens 1 of the embodiment shown in FIGS. 1-2, and whose generally equivalent parts are assigned corresponding primed reference designations, i.e. lens assembly 2', optic 3', haptics 4', 5', anterior surface formation 6', posterior surface formation 7', contact region 8', and contact region plane P', and wherein the roughened surface area 9 defined by the ordered narrow linear furrows or depressions 10 is designated 9a', 9b' and /or 9c', as the case may be.

In this instance, lens assembly 2' includes a generally reduced width oval (or alternatively rectangular) shaped optic 3', which is provided with a pair of laterally disposed light ray modifying or masking slidable wings 11,12, integrally connected thereto, in posteriorly offset or rearward partially overlapping stepped disposition to optic 3', as shown in FIG. 4, for purposes more fully described in said U.S. Pat. No. 4,605,409 to Kelman, the disclosure of which is incorporated herein by reference.

As may be appreciated from FIG. 3a, although optic 3' is generally oval in shape, the included wings 11,12 are of complementary crescent shape to provide lens assembly 2' with an overall generally round or circular composite central shape, i.e. apart from the outwardly flaring haptics 4',5'. At the same time, as is clear from FIGS. 3a and 4, the posteriorly offset disposition of wings 11,12 relative to optic 3+ is such as to provide a space 13 between the posterior surface of optic 3' and the contact region plane P'.

Insofar as pertinent to the present invention, wings 11,12 comprise portions of the contact region 8', and individual roughened surface areas 9a' are located on corresponding portions of contact region 8' on each wings. While three such individual partial areas 9a' in equidistant spaced relation to each other, relative to such round composite central shape, may be distributed on various local sites of the two wings 11,12, it will be understood that, just as in the case of the embodiment of FIGS. 1-2, any number of such local areas 9a' may be provided, optionally with or without the areas 9b' and/or 9c' on the portions of contact region 8' located on haptics 4' and/or 5', or preferably the entirety of the posterior surface of each of the wings 11,12 may contain a corresponding roughened surface area 9a' as contemplated specifically in FIGS. 3a and 3b for enhanced anchoring of lens 1' to the adjacent tissue.

Alternatively, as in the case of the embodiment of FIGS. 1-2, some or all of areas 9a' may be omitted from wings 11,12, and either or both of areas 9b' and 9c' may be included instead on haptics 4' and 5' of lens assembly 2' for analogous results.

FIGS. 5 and 6 show in exaggerated enlarged detail two different configurations of depressions 10 defining a given roughened surface area 9, that of FIG. 5 corresponding to the arrangement of lens assembly 2 of FIGS. 1-2, and that of FIG. 6 corresponding to the arrangement of lens assembly 2' of FIGS. 3a, 3b and 4. However, it will be understood that either the arrangement of FIG. 5 or the arrangement of FIG. 6 may be provided in lens assembly 2 of FIGS. 1-2, or in lens assembly 2' of FIGS. 3a, 3b and 4, or in any other appropriate intraocular lens system, and on any optic, haptic and/or wing or like appendage thereof, interchangeably, or alternatively any other type roughened surface area defining series of ordered narrow linear furrows or depressions may be used, as the case may be, for accomplishing the overall objects and advantages of the present invention.

In this regard, FIG. 5 is directed to a series of side by side linear depressions 10, designated U, which have a generally U-shaped groove cross section, and which are bounded by intervening straight side walls S, whereas FIG. 6 is directed to a series of side by side linear depressions 10, designated V, which have a generally V-shaped groove cross section, and which are bounded by intervening inclined side walls. In either case, it is clear that the corresponding grooves forming the depressions 10 extend generally transversely of the pertinent plane P or P' of the contact region 8 or 8'.

FIG. 7 illustrates one preferred manner of positioning the intraocular lens 1 (or 1') in the eyeball 40. In this connection, the relevant parts of the eyeball 40 include the cornea 41, the iris 42 having an adjustable size central opening or pupil 43 and dividing the adjacent aqueous humor containing interior into an anterior chamber 44 and a posterior chamber 45, and an encapsulated natural eye lens.

In the condition shown in FIG. 7, in accordance with procedures well known to those skilled in the art, the surgeon has already remoed the natural lens and a portion of the anterior wall part of the natural lens capsule 46 via the usual small size corneal incision 41a, leaving intact the posterior wall part 47 of lens capsule 46, which is held in place by the zonules or suspensory ligament and fibers 48 attached to its external periphery. The internal periphery of posterior wall part 47 forms a recessed anterior cul-de-sac or ciliary sulcus 49 which may serve as a seating location for the intraocular lens 1.

Once seated in the posterior chamber, for example in the ciliary sulcus or cul-de-sac 49, the haptics 4,5 of lens 1 naturally urge posterior surface formation 7, and especially contact region 8, against the adjacent surface of tissue of the posterior capsule, for example wall part 47, to assure full coextensive contact seating of lens 1 in place, and particularly of depressions 10 of each roughened surface area 9 in abutment with the vicinal tissue thereat for promoting the desired adhesion connection.

In the analogous case where other appendages may be present, such as wings 11,12 in the case of lens 1', these will be pressed in place in a like manner, to assure that all roughened surface areas 9, regardless of their location on the particular lens assembly, will be brought into abutment with the vicinal tissue of the adjacent portion of the posterior capsule, as for example the posterior wall part 47.

FIG. 8 indicates the disposition of the vicinal tissue T of the posterior wall part 47 in the U-shaped grooves forming the individual furrows or depressions 10 of the particular roughened surface area 9, a condition which surprisingly develops within a matter of only a few hours after completion of the seating of lens 1 (or 1'), pressed in place against posterior wall part 47. It is clear that the tissue enters or grows into, and distributes itself along, the comparatively minute width and pronounced transverse length, i.e. depth, of each of the series of ordered narrow linearly extending depressions 10, for accelerated adhesion to the receptive interior surfaces of the grooves or depressions and enhanced anchoring of the intraocular lens to such adjacent tissue, e.g. the posterior wall part 47.

In particular, the connection interface between the depressions 10 of roughened surface area 9 and the adjacent tissue of posterior wall part 47 is one which inherently constitutes a surface adhesion type bonding, rather than a mechanical rivet type gross connection, and one which enables the tissue to become adhered to the internal surface expanse of the depressions 10 in comparatively rapid manner, rather than by slow ingrowth accumulation as a relatively large volume mass sufficient to fill out and engage the full cross section as well as the axial length of provided through holes for anchoring purposes as previously suggested by the art (cf. said U.S. Pat. No. 3,458,870 to Stone, Jr. and said U.S. Pat No. 4,304,012 to Richard).

A distinct feature and advantage of the present invention is that the roughened surface area 9 is defined by a series of ordered side by side narrow linearly extending furrows or depressions, such that they collectively reinforce one another in anchoring the lens assembly to the vicinal tissue, such as that of posterior wall part 47.

It will be understood that such "roughened" surface area is one which is not only unpolished, as distinguished from a polished or optically ground light ray transmitting surface region of an optic, but also one which has been deliberately made less smooth than even the starting surface of the optic prior to its being polished, by affirmatively providing a series of ordered narrow linear furrows or depressions therein according to the present invention.

As the artisan will appreciate, any appropriate means may be used to impart the roughened surface area onto the contact region site. For example, the side by side linear depressions or furrows may be provided by scoring, grinding or like conventional operations, directed at the local surface region or regions where the depressions are to be located.

Because the ordered series necessarily provides an internal groove connection site, collectively of several orders of magnitude increase in surface area over the basic surface area of the corresponding contact region portion containing the given roughened surface area, i.e. in the direction of its plane P (or P'), the potential contact surface extent offered to the vicinal tissue for adhesion is correspondingly increased, so as to assure the desired surface adhesion connection in situ throughout the areal extent of the given roughened surface area.

It will be seen from FIGS. 5 and 6 that, regardless of the groove shape, the depth of each depression 10 far exceeds the dimension across its entrance, and more than twice the value of the pronounced dimension of this depth (i.e. comprising at least the additive total depth extent of the two side walls bounding the given depression apart from the extent of the width therebetween) is multiplied by the running length of the given linear furrow or depression to obtain the total internal roughened surface area available for receptive adhesion contact by the vicinal tissue.

Under such conditions, the extraordinarily large potential surface area available for the contemplated adhesion contact is sufficient to achieve in a comparatively short period of time a fully bonded connection at the composite connection interface provided, which is adequate to inhibit accidental or otherwise caused dislodgment or slippage of the intraocular lens from its intended optical alignment position.

This is true not only where the disturbing force, e.g. the rubbing of one's eye, is exerted in a perpendicular direction, i.e. crosswise of the ordered series of depressions, wherein because of their transverse orientation the depressions readily withstand such perpendicular force, but more significantly this is also true where the disturbing force is exerted in a direction parallel to the linear alignment direction of the ordered series of depressions. Specifically, in the latter situation, the depressions readily withstand such a parallel disturbing force, because of the very nature and extent of their comparatively immense cumulative recessed contact surface area, densely packed in a relatively small portion of the contact region.

Moreover, due to the comparatively minute dimensions inherently involved in relation to the necessarily small finite dimensions of the intraocular lens itself, the adhesion of the vicinal tissue to the depressions at the connection interface site is beneficially free from undesired gross stress and does not result in irritation of the vicinal tissue or adjacent parts of the eye.

It has been found as well that the posterior wall part of the posterior capsule more readily adheres to the roughened surface area according to the present invention than to a smooth surface, such that the vicinal tissue acts to fixate the intraocular lens in position within a short finite time span, of at most a few hours, and in turn prevents the lens from being dislodged. This enhanced adhering tendency regarding the roughened surface area depressions, as opposed to a smooth surface, appears to occur independently of the surface property of some plastics such as silicone which promote collection of materials of the eye such as fibrin thereon, or of the opposite property of other plastics such as polymethylmethacrylate which inhibit collection of such eye materials thereon.

Advantageously, in this regard, the roughened surface area should desirably amount to a total of at least about 2 $mm^2$ in areal extent, and should contain, for example, about 40–120 side by side linear depressions per millimeter. The depressions should preferably be of a depth of at least about 0.01 mm up to a maximum of about one half of the thickness of the structure constituting the portion of the contact region at which the roughened surface area is provided. For example, the depressions may be about 0.01–0.12 mm in depth, and the host structure containing the contact region may have a corresponding thickness of only about 0.25 mm.

Where a plurality of individual roughened surface areas is contemplated, such as at least three individual segment like arcs of an interrupted annulus extending peripherally around the optic of the lens assembly, or the like, these are preferably provided in equidistant spaced relation to each other, for example with each arc being at least about 1 mm² in areal extent.

It will be realized that the intraocular lens may have any desired shape and contain any appropriate optical elements, with or without collateral appendages such as haptics, light masking wings, or the like, so long as it includes at least one roughened surface area defined by a series of ordered narrow linear depressions appropriately located thereon in accordance with the present invention.

Preferably, however, the lens assembly will be made of polymethylmethacrylate (PMMA), and include an optic, haptics, and slidable wings. For example, the optic may be provided with a thickness of about 1.5 mm, and a diameter of about 3 mm, and include slidable or foldable wings which are deformable so that the assembly can be inserted through a minimum size corneal incision, for example of only about 3 mm length, after which the composite lens can be allowed to expand to its original size and undeformed state, while retaining its desired optical characteristics, for appropriate seating in the eye by the surgeon, in the above described manner.

In such preferred embodiment, the wings are positioned adjacent to the posterior face of the optic and are slidable along such face. Specifically, the posterior face of each of the wings is positioned posteriorly of the posterior face of the optic so that the wings assume a space between the optic and the posterior capsule wall when the lens is seated. Preferably, the roughened surface according to the present invention is located on the posterior face of the wings.

The intraocular lens may be formed of any suitable light focusing optic serving material. Of course, any such material must be compatible with the eye fluid environment in the interior of the eyeball, for instance a non-toxic plastic, including in particular a plastic such as silicone, or polymethylmethacrylate (PMMA), or the like, with any associated haptic or the like position fixation members, wings, or the like, being of the same type material, or in the case of such position fixation members even a comparatively more flexible material than silicone, such as polypropylene.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Intraocular lens for implantation in the posterior chamber of an eye, following extracapsular removal of the natural eye lens, which comprises
 a lens assembly constructed of a non-hydrophillic material having an anterior formation and a posterior surface formation, at least a portion of the posterior surface formation constituting a planar contact region adapted to be seated against the adjacent tissue surface of a part of the posterior capsule to form a connection interface for anchoring of the lens assembly thereat,
 the contact region being provided with at least one roughened surface area defined by a series of ordered narrow curvilinear depressions therein extending generally transversely of the plane of the contact region and containing about 40-120 side by side curvilinear depressions per millimeter, for accelerated adhesion of the tissue of the adjacent posterior capsule part to the depressions and enhanced anchoring of the lens assembly to the posterior capsule part, to prevent dislodgment of the implanted intraocular lens.

2. Lens of claim 1 wherein a plurality of said roughened surface areas is provided at corresponding spaced apart local sites on the contact region.

3. Lens of claim 1 wherein the lens assembly includes an optic comprising the contact region, and the at least one roughened surface area is located on the contact region at the periphery of the optic.

4. Lens of claim 3 wherein the roughened surface area is in the shape of an annulus extending peripherally around the optic.

5. Lens of claim 3 wherein the roughened surface area is in the shape of individual spaced apart segment like arcs of an interrupted annulus extending peripherally around the optic.

6. Lens of claim 5 wherein at least three said arcs are provided in equidistant spaced relation to each other.

7. Lens of claim 6 wherein the roughened surface area of each arc is at least about 1 mm² in areal extent.

8. Lens of claim 1 wherein the lens assembly includes an optic provided with a pair of opposed haptics comprising portions of the contact region, and at least one said roughened surface area is located on a corresponding contact region portion of each haptic.

9. Lens of claim 1 wherein the lens assembly includes an optic provided with a pair of laterally disposed light ray modifying wings comprising portions of the contact region, and at least one said roughened surface area is located on a corresponding contact region portion of each wing.

10. Lens of claim 1 wherein the at least one roughened surface area is of a total of at least about 2 mm² in areal extent.

11. Lens of claim 1 wherein the roughened surface area depressions are of a depth of at least about 0.01 mm up to a maximum of about one half of the thickness of the structure constituting the portion of the contact region at which the roughened surface area is provided.

12. Lens of claim 1 wherein the roughened surface area depressions are of about 0.01-0.12 mm in depth.

13. Lens of claim 1 wherein the at least one roughened surface area is of a total of at least about 2 mm² in areal extent, and contains about 40-120 side by side linear depressions per millimeter, each depression being about 0.01-0.12 mm in depth.

14. Lens of claim 1 wherein the lens assembly includes an optic provided with a pair of spaced wing portions located posteriorly of said optic and comprising portions of the contact region, and each said wing portion includes at least one said roughened surface area.

15. Intraocular lens for implantation in the posterior chamber of an eye, following extracapsular removal of the natural eye lens, which comprises
 a lens assembly constructed of a non-hydrophillic material having an anterior surface formation and a posterior surface formation, at least a portion of the posterior surface formation constituting a planar contact region adapted to be seated against the adjacent planar tissue surface of a part of the posterior capsule to form a connection interface for anchoring of the lens assembly thereat, the contact region being provided with at least one roughened surface area defined by a series of ordered narrow linear depressions therein extending generally transversely of the plane of the contact region, and containing about 40-120 side by side linear depressions per millimeter, for accelerated adhesion of the tissue of the adjacent posterior capsule part to the depressions and enhanced anchoring of the lens assembly to the posterior capsule part, to prevent dislodgment of the implanted intraocular lens, said posterior surface formation being made of a material having the eye tissue bonding adhesion characteristics of polymethylmethacrylate, silicone or polyethylene.

* * * * *